United States Patent
Tolkoff et al.

(10) Patent No.: US 7,255,691 B2
(45) Date of Patent: Aug. 14, 2007

(54) CHEMILUMINESCENT LIGHT SOURCE USING VISIBLE LIGHT FOR BIOTHERAPY

(75) Inventors: Marc Joshua Tolkoff, Brookline, MA (US); Philip Levin, Thompson, CT (US); Robert Arcangeli, Westborough, MA (US); Andy Levine, Newton, MA (US); Thomas G. Chasteen, Huntsville, TX (US)

(73) Assignee: LumeRX Inc., Boston, MA (US)

( * ) Notice: Subject to any disclaimer, the term of this patent is extended or adjusted under 35 U.S.C. 154(b) by 417 days.

(21) Appl. No.: 10/414,824

(22) Filed: Apr. 16, 2003

(65) Prior Publication Data
US 2004/0010299 A1   Jan. 15, 2004

Related U.S. Application Data

(60) Provisional application No. 60/372,695, filed on Apr. 16, 2002.

(51) Int. Cl.
    *A61B 18/18* (2006.01)
(52) U.S. Cl. .................. 606/9; 606/3; 606/10; 607/88; 362/34; 362/84; 313/483
(58) Field of Classification Search .............. 606/3–26; 607/88–93; 362/34, 84; 313/483–490
See application file for complete search history.

(56) References Cited

U.S. PATENT DOCUMENTS

| 3,940,605 A | * | 2/1976 | Gerber ..................... 362/34 |
| 3,984,786 A | | 10/1976 | Pike ......................... 331/94.5 |
| 4,583,526 A | | 4/1986 | Ali |
| 4,814,949 A | | 3/1989 | Elliott |
| 4,830,460 A | | 5/1989 | Goldenberg |
| 4,889,129 A | | 12/1989 | Dougherty et al. |
| 4,998,930 A | | 3/1991 | Lundahl |
| 5,104,392 A | | 4/1992 | Kittrell ..................... 606/15 |
| 5,192,278 A | | 3/1993 | Hayes et al. |
| 5,329,938 A | * | 7/1994 | Lonky ....................... 600/223 |
| 5,334,171 A | | 8/1994 | Kaldany |
| 5,399,583 A | | 3/1995 | Levy et al. |
| 5,405,369 A | | 4/1995 | Selman et al. |
| 5,445,608 A | | 8/1995 | Chen et al. ................. 604/20 |
| RE35,132 E | * | 12/1995 | Bay et al. .................... 362/34 |

(Continued)

FOREIGN PATENT DOCUMENTS

DE   502 669   7/1930

(Continued)

OTHER PUBLICATIONS

Wells, H.G., et al., "The Science of Life", The Literary Guild, 1934, pp. 1086-1088.

(Continued)

*Primary Examiner*—A. Farah
(74) *Attorney, Agent, or Firm*—Mills & Onello, LLP

(57) ABSTRACT

The present invention relates to a devices and methods for killing and/or debilitating pathogenic microorganisms in or on a patient's body, such as light-sensitive bacteria including *helicobacter pylori* and/or *propionibacterium acnes*. A chemiluminescent light source provides electromagnetic radiation having predetermined wavelengths in the visible spectrum. The light wavelengths are selected for absorption by naturally-occurring photosensitive chemicals produced by the patient's body.

4 Claims, 8 Drawing Sheets

U.S. PATENT DOCUMENTS

| | | | |
|---|---|---|---|
| 5,531,662 | A | 7/1996 | Carr |
| 5,653,683 | A | 8/1997 | D'Andrea |
| 5,671,998 | A | 9/1997 | Collet ................... 362/101 |
| 5,800,478 | A | 9/1998 | Chen et al. |
| 5,817,144 | A | 10/1998 | Gregory |
| 5,845,640 | A * | 12/1998 | Lawandy ................ 600/473 |
| 5,855,595 | A | 1/1999 | Fujishima |
| 5,871,522 | A | 2/1999 | Sentilles |
| 5,876,427 | A | 3/1999 | Chen et al. |
| 5,913,883 | A * | 6/1999 | Alexander et al. ............ 606/9 |
| 5,993,378 | A | 11/1999 | Lemelson ................. 600/109 |
| 6,143,019 | A | 11/2000 | Motamedi et al. |
| 6,183,773 | B1 | 2/2001 | Anderson |
| 6,235,148 | B1 * | 5/2001 | Courson et al. ........ 156/379.6 |
| 6,254,594 | B1 * | 7/2001 | Berry ....................... 607/88 |
| 6,335,465 | B1 | 1/2002 | Golub |
| 6,443,978 | B1 | 9/2002 | Zharov ..................... 607/91 |
| 6,464,625 | B2 | 10/2002 | Ganz |
| 6,491,618 | B1 | 12/2002 | Ganz |
| 6,497,181 | B1 * | 12/2002 | Manole et al. ............ 102/513 |
| 6,602,274 | B1 | 8/2003 | Chen |
| 6,685,331 | B1 | 2/2004 | Rockwell |
| 6,764,501 | B2 * | 7/2004 | Ganz ......................... 607/92 |
| 2004/0073278 | A1 | 4/2004 | Pachys |

FOREIGN PATENT DOCUMENTS

| | | |
|---|---|---|
| DE | 502 669 C | 7/1930 |
| JP | 10-094583 | 4/1998 |
| WO | 98/32370 | 7/1998 |
| WO | WO 98/32370 | 7/1998 |
| WO | WO 00/64537 | 11/2000 |
| WO | WO 03/082372 A2 * | 10/2003 |

OTHER PUBLICATIONS

Hoare, C.A., "Handbook of Medical Protozoology", Balliére, Tindall and Cox, 1949, pp. 77-78.

Lee, W.S., et al., "Comparative Studies of Porphyrin Production in *Propionibacterium acnes* and *Propionibacterium Granulosum*", Journal of Bacteriology, vol. 133, No. 2, American Society for Microbiology, Feb. 1978, pp. 812-815.

Kjeldstad, B. and A. Johnson, "An Action Spectrum for Blue and Near Ultraviolet Inactivation of *Propionibacterium acnes* with Emphasis on a Possible Porphyrin Photosensitization", Photochemistry and Photobiology vol. 43, No. 1, Pergamon Press, 1986, pp. 67-70.

Martinetto, P., et al., "Bactericidal Effects Induced by Laser Irradiation and Haematoporphyrin Against Gram-Positive and Gram-Negative Microorganisms", Bioscience Ediprint Inc., 1986, pp. 335-342.

Kubey, W. and C.J. Holmes, "In vitro Studies on the Microbicidal Effectivenss of a Xenon-Based Ultraviolet Light Device for Continuous Ambulatory Peritoneal Dialysis Connections", Blood Purification vol. 9, Karger, Sep. 1991, pp. 102-108.

Futsaether, C.M., et al., "Intracellular pH changes induced in *Propionbacterium acnes* by UVA radiation and blue light", Journal of Photochemistry and Photobiology vol. 31, Elsevier, 1995, pp. 125-131.

Millson, C.E., et al., "The Killing of *Helicobacter pylori* by low-power laser light in the presence of a photosensitiser", Journal of Medical Microbiology vol. 44, The Pathological Society of Great Britain and Ireland, 1996, pp. 245-252.

Millson, C.E., et al., "Ex-vivo treatment of gastric Helicobacter infection by photodynamic therapy", Journal of Photochemistry and Photobiology vol. 32, Elsevier, 1996, pp. 59-65.

Sigurdsson, V., et al., "Phototherapy of *Acne vulgaris* with Visible Light", Dermatology vol. 194, Karger, 1997, pp. 256-260.

Papageorgiou, P., et al., "Phototherapy with blue (415 nm) and red (660 nm) light in the treatment of Acne vulgaris", British Journal of Dermatology vol. 142, British Association of Dermatologists, 2000, pp. 973-978.

Hongcharu, W., et al., "Topical ALA-Photodynamic Therapy for the Treatment of Acne vulgaris", The Society of Investigative Dermatology, Inc., 2000.

Shalita, A.R., et al., "Acne Photoclearing (APC) Using a Novel, High-Intensity, Enhanced, Narrow-Band, Blue Light Source", Clinical Application Notes vol. 9 No. 1.

Moretti, M., "Light-based systems shown to be effective in treating active acne", The BBI Newsletter, American Health Consultants, Mar. 2002, pp. 72-73.

Cunliffe, W.J., and V. Goulden, "Phototherapy and Acne vulgaris", British Journal of Dermatology vol. 142, No. 5, British Association of Dermatologists, May 2000, pp. 855-856.

* cited by examiner

Curve of H.pylori colony forming units vs light deliver of different wavelengths, showing that the blue/violet range is most effective.

CHEMILUMINESCENT LIGHT SOURCE USING VISIBLE LIGHT FOR BIOTHERAPY

CROSS-REFERENCE TO RELATED APPLICATIONS

This application incorporates by reference, and claims priority to and the benefit of U.S. Provisional Patent Application No. 60/372,695, filed on Apr. 16, 2002.

FIELD OF THE INVENTION

This invention relates to light source therapy of tissue and/or biological material on or within a patient's body and, more particularly, to light source therapy using chemiluminescent light sources.

BACKGROUND OF THE INVENTION

Many afflictions, diseases, and/or general disorders suffered by humans and animals can be successfully treated with light therapy. Some of these light-treatable afflictions relate to biological cells, organisms, tissues residing on and/or within a patient's body. For example, light is known to be effective in the treatment of the skin condition acne vulgaris. Acne vulgaris is due, at least in part, to inflammations caused by infections of propionibacterium acnes (P. acnes). Other applications include the treatment of inflammation, and killing and/or debilitating other bacteria capable of causing infection, such as helicobacter pylori (H. pylori).

H. pylori is a bacterial pathogen that infects the stomach and duodenum, today representing one of the most common gastrointestinal infections in the world. In industrialized nations, such as United States, H. pylori may be found in 20% or more of the adult population. It is a chronic gut infection and, once acquired, is notoriously difficult to eradicate. Although most infectious bacteria can be readily destroyed by the human immune system, H. pylori is relatively resistant to a host immune response, even if vigorous. At least one reason for H. pylori's resistance relates to its residing within the lining of the stomach and on the surfaces of the stomach and duodenal cells.

Effective light therapy, generally, includes an initial pretreatment of the tissue of interest with a photosensitizer. In one example, PhotoDynamic Therapy (PDT) refers to the therapeutic treatment of a portion of a patient's body using light. As an initial step, PDT includes delivering a sensitizing drug to a treatment site of a patient's body. This step is then followed by illumination of the treated area to activate the sensitizing drug.

PDT light sources are typically powered by high-powered sources, such as electrical power source. Light sources include, for example, fluorescent lights, incandescent lights, light emitting diodes, and lasers. Thus, during PDT, a light source, such as an electrical lamp, is shone upon a treatment site for a period of time sufficient to deliver a dosage amount (e.g., a total amount of energy). There are other means for creating light of specific wavelengths. In addition to standard light sources, many exothermic chemical reactions produce at least some of their energy in the form of photons of specific wavelengths. For example, combustion is one form of chemical reaction that produces photons, the i.e., "flame." Furthermore, the wavelength of the photons produced are observed in the color of the flames.

SUMMARY OF THE INVENTION

The present invention allows for effectively treating ailments and afflictions of biological cells, organisms, tissues, etc., without having to apply a sensitizing drug, by taking advantage of naturally-occurring chemicals produced by the body and disposed within and around the treatment site. The invention is useful in the treatment of various parts of the body (e.g., the mouth, the stomach, bowel, lungs, peritoneal cavity, urinary tract, nasal cavity, ear canal, etc.), and is also particularly useful in the treatment of the skin. Namely, the invention is particularly effective in treating bacterial infections, such as chronic infections of the gut caused by H. pylori and infections of the skin, such as acne vulgaris, caused by P. acnes, by killing and/or debilitating the respective bacteria. The present therapeutic method involves the use of light for treating a part of a patient's body, for example, by eliminating pathogenic microorganisms within the body or supported upon the surface, e.g., the face.

In one aspect, the invention relates to a device for killing and/or debilitating pathogenic microorganisms, such as P. acnes and/or H. pylori, in or on a body. The device includes a chemiluminescent light source that provides electromagnetic radiation having predetermined wavelengths in the visible spectrum. The chemiluminescent light source is selected to produce light at wavelengths suited for absorption by naturally-occurring photosensitive chemicals produced by a patient's body. In one embodiment, the predetermined wavelengths are selected to reside substantially within the spectral region including 400 to 600 nanometers.

In one embodiment, the chemiluminescent light source includes an energizer producing a selected amount of energy for a selected duration. The light source further includes a wavelength-selectable material energetically coupled to the energizer. The chemiluminescent light source can be a liquid. The wavelength-selectable material produces electromagnetic radiation in response to the energy coupled from the energizer. The electromagnetic radiation is sustained at one or more selected wavelengths for the selected duration.

In another embodiment, the chemiluminescent light source further includes a first reservoir for initially containing the wavelength-selectable material. The first reservoir can be electromagnetically coupled to a treatment site. The light source also includes a second reservoir containing the energizer. The first and second reservoirs are coupled together using a nozzle. Finally, the light source includes means for transporting at least a portion of the energizer from the second reservoir to the first reservoir through the nozzle. The nozzle can be an adjustable nozzle, as in an adjustable spray nozzle.

In some embodiments, the wavelength-selectable material includes a dye, and the energizer includes an energy-releasing chemical reaction. For example, the energy-releasing chemical reaction can include a fuel-oxidant mixture, such as an oxalate and a peroxide that, when mixed together, release energy.

The device can include a delivery element containing at least a portion of the chemiluminescent light source, the device elements being adapted for providing at least a portion of the electromagnetic radiation to a treatment site. The delivery element can include a pad adapted for placement upon the skin of a patient, the pad selectively delivering electromagnetic radiation to the skin. The delivery element can include a mask for placement upon the face of a patient.

In another embodiment, the device further includes a first reservoir containing a first portion of a liquid electromagnetically coupled to a treatment site, and a second reservoir containing a second portion of the liquid remotely located from the treatment site. The first and second reservoirs are coupled together via a tube. The device also includes means for transporting at least some of the first portion of the liquid from the first reservoir through the tube to the second reservoir.

In another aspect, the invention relates to a process for killing and/or debilitating pathogenic microorganisms, such as *P. acnes* and/or *H. pylori*, in or on a body. The process includes providing a chemiluminescent light source that generates a chemiluminescent reaction to produce electromagnetic radiation at predetermined wavelengths in the visible spectrum. The process also includes illuminating the pathogenic microorganisms with electromagnetic radiation from the chemiluminescent light source for a selected treatment period. As a result, at least some of the microorganisms in or on the body are killed and/or debilitated.

The process can include providing an energizer that produces a selected amount of energy. The energizer can be provided over a selected period of time. A wavelength-selectable material, such as a dye, is also provided and selectively coupled to the energizer to produce electromagnetic radiation in response to the coupled energy. As described above, the radiation can be provided at one or more selected wavelengths for the selected period of time.

In yet another aspect, the invention relates to a device for killing and/or debilitating bacteria, such as *P. acnes* and/or *H. pylori*, in or on a patient's body. The device includes a chemiluminescent light source for providing electromagnetic radiation having wavelengths substantially within the visible spectral region comprising about 400 to about 690 nanometers. The wavelengths can be selected for selectively disabling the bacterium.

In still another aspect, the invention relates to a process for killing and/or debilitating bacteria, such as *P. acnes* and/or *H. pylori*, in or on a patient's body. The process includes providing a chemiluminescent light source that generates a chemiluminescent reaction to produce electromagnetic radiation substantially within the spectral region comprising about 400 to about 690 nanometers. The process also includes illuminating the bacteria with electromagnetic radiation from the chemiluminescent light source for a selected treatment period to thereby kill and/or debilitate the bacteria in or on the body.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION OF THE INVENTION

Figure 1:
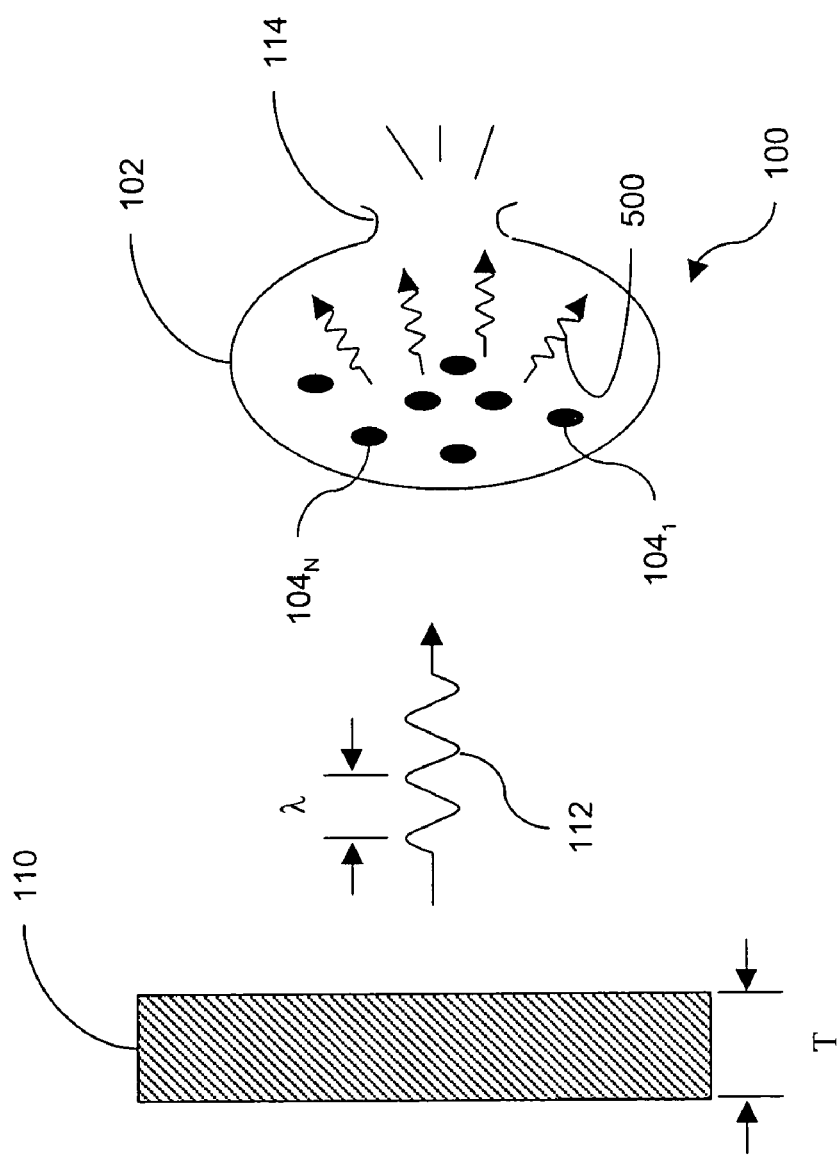
FIG. 1 is a schematic diagram of one exemplary embodiment of the invention including a chemiluminescent light source treating an organism.

At least one advantage of the present invention includes an ability to kill and/or debilitate light-sensitive pathogenic microorganisms, such as *P. acnes* or *H. pylori*, using visible light. As few organisms, including few human cells, are sensitive to visible light, the bacteria can be killed by the visible light mediated necrosis without serious destruction of the host cells. At least one further advantage of chemiluminescent treatments includes their ability to transport a light-emitting liquid to a treatment site that would otherwise be difficult to reach and/or illuminate with conventional light sources. For example, a light-emitting liquid can be provided to a location inside a patient's body through a relatively small opening. The small opening can be a percutaneous opening, and/or a naturally-occurring body lumen. For example, the light-emitting liquid can be passed to a patient's gut through the esophagus, to a bladder through the urethra, and to a kidney through the ureter. A light emitting liquid is also well adapted for illuminating completely complex and/or convoluted spaces, such as the inside of a stomach with its folds, or rugae, and the inside of the mouth with its teeth and tongue.

Additionally, chemiluminescent light sources provide relatively large amounts of light energy without creating significant amounts of heat. Further, the reaction rate of the chemiluminescence is selected to be slow or fast, for example, based on the proper selection of chemical constituents, and/or flow rates of the chemiluminescent light source past a treatment site. Being able to vary the rate of the reaction to control the release of light energy is important, because some treatments are more effective with slow, low power illumination; whereas, others are more effective with fast, high power illumination. Thus, chemiluminescence allows for greater flexibility in treatment variations specifically suited to a particular organism, tissue, organ or biological system.

Chemiluminescence is the production of photons from a chemical reaction. The light from chemiluminescence is typically used for activating a photosensitive drug. The exact mechanism of action of light therapy generally depends on the organism or tissue being treated. Certain bacteria produce and/or concentrate chemical substances that behave in a similar fashion to sensitizing drugs when illuminated with the wavelength of light that they absorb. These "endogenous" chromophores naturally produced and/or concentrated within bacteria can be a form of porphyrins. For example, some bacteria produce and/or concentrate porphyrins, such as protoporphyrin or cuproporphyrin, that absorbs electromagnetic radiation within the wavelengths of light around 400, 507, 540, 590, and 635 nanometers (nm) among other wavelength regions.

In general, the treatment disclosed herein can be applied to microorganisms residing on and/or in the epithelium of any other passage or lumen. During treatment, electromagnetic radiation having wavelengths in the visible spectrum (i.e., visible light) reacts with naturally produced and/or concentrated "endogenous" chromophores (porphyrins). In at least one advantageous effect, the light in combination with the porphyrin produces necrosis or cell death evidenced by the microorganism's inability to divide. This advantageous effect may be due, in part, to the light inducing a secondary effect of upon the microorganism, namely, the excited porphyrins releasing free radicals including oxygen that damage the bacteria and result in necrosis. An advantage of the invention lies in the fact that few organisms and few human cells are sensitive to visible light, so the microorganism being treated (e.g., *H. pylori*) can be killed without substantially damaging the surrounding tissue. Accordingly, the bacteria can be killed by visible light mediated necrosis without serious destruction of the host cells.

For *H. pylori*, the endogenously produced porphyrins have a very strong absorption peak in the 405+/−25 nm range, with smaller peaks at about 505, 550, 570, and 655 nm. Light delivered at a sufficient dosage in these narrow wavelengths, or in a broad band including the wavelengths of these absorption peaks, e.g., 400–650 nm, kills and/or debilitates the bacteria, without added drugs or chemicals. The treatment is most effective along the surface, but can also be effective beneath the surface, generally having decreasing benefit with increasing penetration into the body tissue. The penetration of light into tissue varies with wavelength, with greater penetration occurring at longer wavelengths. For example, light at a wavelength of 400 nm penetrates approximately 1 millimeter (mm) or so, while 650 nm light penetrates approximately 3 mm or more. Thus, the wavelength of light can be selected to optimize a desired depth of penetration. Notwithstanding the depth of penetration, a particularly effective wavelength for killing and/or debilitating *H. pylori* is approximately 400 nm. Additionally or alternatively, using electromagnetic radiation having multiple wavelengths within the visible spectrum (i.e., multicolored light) can be used to provide both effective and deeper therapeutic effect. Total eradication of the microorganism can be claimed with a 2–3 $\log_{10}$ (i.e., 99%–99.9%) reduction of bacteria colony count, as the host immune system response can generally overcome any remaining bacteria.

Additionally, certain wavelengths of light, such as red light around 660 nm (630–690 nm), have an anti-inflammatory effect on tissue. This anti-inflammatory effect can aid by enhancing a patient's healing response and/or diminish inflammation. Thus, treatment of an inflammation, for example, caused by an *P. acnes* infection on a patient's skin, can include both red and blue/violet light. The blue/violet light eradicating the bacteria and the red light has a beneficial effect on the inflammation of the skin.

The present invention relates to Photo therapy (PT) including the treatment of biological system, organism, tissue and the like with light. It is not necessary to combine the light with any sensitizing chemicals or drugs, as the light acts upon naturally-occurring chemicals produced within a patient's body to provide the beneficial effect. However, in some embodiments, sensitizing chemicals or drugs can be added to a treatment before and/or during application of the treating light to further enhance the beneficial effect.

One embodiment of a chemiluminescent light source for treating biological tissue, organisms, or materials is illustrated in FIG. 1. For example, a biosystem 100, such as an organism 102 (e.g., bacteria, such as *P. acnes* or *H. plyori*), includes naturally-occurring chemicals, such as porphyrins 104. Photo therapy of a portion of a patient's body including such biosystem 100 can be accomplished using a chemiluminescent material 110. The chemiluminescent material 110 emits electromagnetic radiation 112 having one or more spectral components, each representable by corresponding wavelength ($\lambda$). Primarily, the radiation 112 occurs within the visible spectrum corresponding to a wavelength range from about 400 nm, to about 690 nm. In some embodiments, visible light can be combined with electromagnetic radiation from other parts of the spectrum, for example from the ultraviolet (UV) spectrum and/or from the infrared (IR) spectrum to further enhance, or supplement the treatment. The beneficial effect of illumination by the chemiluminescent material 110 may be due, at least in part, to a secondary effect produced by the naturally-occurring chemicals produced by the body, such as free radicals produced by excited porphyrins. The treatment results in the damage 114 and/or debilitation of at least some of the cells 102, and/or microorganisms, generally disposed within the treatment site.

The light source is developed using chemiluminescent technologies. Chemiluminescence is a chemical reaction that emits light. One example includes two (or more) chemicals in liquid form mixed together. The resulting chemical reaction emits light of specific wavelengths and releases a total amount of energy per unit volume. In some embodiments, the chemicals contain both a dye that creates the specific wavelengths of light and an energy-releasing reaction species, referred to as an energizer, providing the energy required to "pump" the dye molecules to a higher energy state. When the dye molecule naturally relaxes from its higher energy state, a photon of a specific wavelength is released. In some embodiments, the dye can include multiple components, for example, a blend of dyes creating multiple wavelengths, or bands of wavelengths. In other embodiments the chemicals contain luminol (e.g., $C_8H_7O_3N_3$) combined with an energizer. The energizer can be a solution of hydrogen peroxide, a hydroxide, and optionally one or more catalysts, such as iron.

The proper selection of the chemicals can provide light of a specific wavelength peak, or by combining multiple chemicals with different dyes light of multiple peaks can be delivered. In addition, the chemicals providing the energy-supplying reaction can be selected to be a rapid, very energetic reaction or a longer, slower and less energetic reaction. If one desires a low light intensity for a long time, the chemicals should be selected for a slow reaction rate. Conversely, for high intensity, the chemicals for a fast reaction should be used. The total number of photons delivered depends on the energy produced by the reaction, the efficiency of the reaction in exciting the dye to its higher energy state, and the efficiency in photon emission by the excited dye molecules relaxing to their lower energy state. The brightness of the illumination and the duration of the light are dependent on first order chemical reaction kinetics. That is, heating up the chemicals makes the reaction rate faster, approximately twice as fast for a 10 degree centigrade increase in temperature.

The chemiluminescent material 110 can be prepared as a liquid for topical applications and, where nontoxic, for internal applications, such as an oral rinse, or a cocktail for ingestion. Alternatively, the chemiluminescent material 110 can be prepared as a cream or salve, particularly well suited for topical application, as the material 110 tends to remain in the general region where initially applied. Further, the intensity of the emitted light from the chemiluminescent material 110 is controlled, to some extent, by the material's 110 surface-to-volume ratio. Generally, the chemiluminescent material 110 is prepared to cover a surface area defined by the area of the treatment site. The material 110 also has a thickness, T, that is relatively thin in relation to the surface area. If the thickness of the chemiluminescent material 110 is too great, some of the emitted light will be absorbed by the material itself.

Figure 2A:
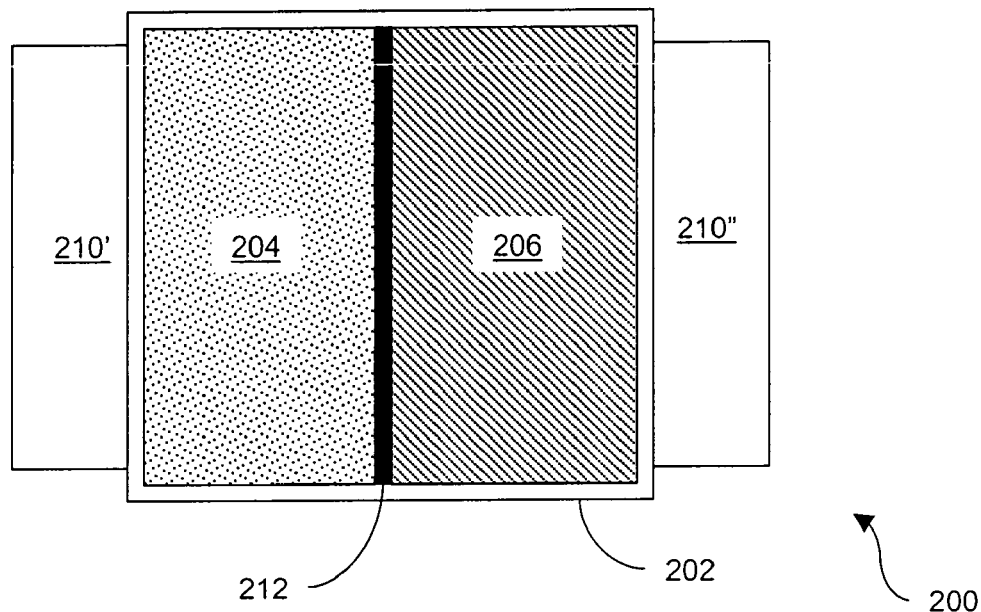
FIGS. 2A and 2B are a schematic diagrams showing a top view and cross-sectional side view of an embodiment of the invention including a chemilumiscent applicator.

Special bandages containing reservoirs of chemical may be affixed to the body adjacent to the wound for light therapy. In one embodiment, chemiluminescent material 110 is disposed within a flexible container, such as a pad, adapted for treating a portion of a patient's body. FIG. 2A illustrates one embodiment of a chemiluminescent applicator pad 200. The pad 200 includes a chemiluminescent applicator housing 202 defines one or more reservoirs within which the chemiluminescent mixture is disposed.

The applicator housing 202 can be constructed, for example, using a front sheet 208 and rear sheet 209 welded, glued, or otherwise sealed about their perimeters. The sheet materials can include nylon 6-6, PVC, PET, or other translucent polymers. Optionally, the sheet material can include a translucent "window" region in an otherwise opaque sheet, thereby tailoring the light-emitting region. The rear sheet 209, away from the treatment site, can be opaque to light, or reflective to reflect light back toward the front sheet 208, and the treatment area.

In some embodiments, the chemiluminescent material is prepared by mixing two or more component materials to initiate the chemiluminescent effect upon demand. Accordingly, the applicator housing 202 can be initially prepared having two separate reservoirs separated by a barrier 212. One of the reservoirs generally contains a first component material 204, i.e., a dye. The other of the reservoirs contains a second component material 206, such as an energy-releasing reaction species, adapted for energizing the wavelength selectable material to emit light. The barrier 212 is advantageously prepared as a breakable membrane that can be broken by the user, thereby causing the mixing of the two component materials 204, 206 and initiating the chemiluminescent effect.

Figure 2B:
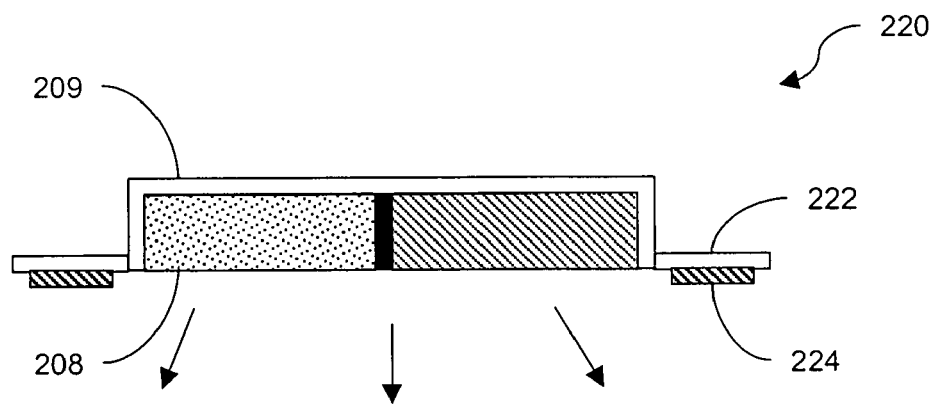

The chemiluminescent applicator pad 200 can optionally include fastening members 210', 210" (generally 210) adapted to fasten the pad 200 to a portion of a patient's body. The fastening members 210 can include tabs, or flaps that can be secured to the patient, for example, with a pressure sensitive adhesive tape or bandage. The tabs 210 can also include a strap, such as an elastomeric strap, or strings. Referring to a cross-sectional schematic view of an alternative embodiment of a pad 220 shown in FIG. 2B, the tabs 210 themselves can include a securing compound, such as a pressure sensitive adhesive, or glue.

Figure 3A:
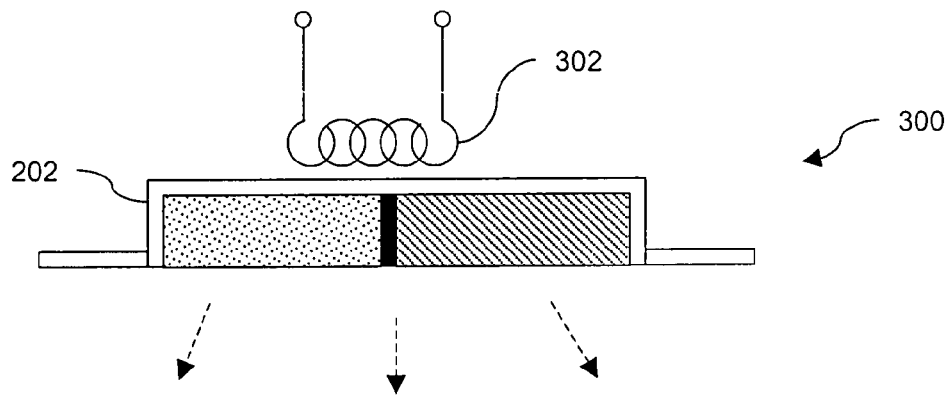
FIGS. 3A–3C are schematic cross-sectional side view diagrams of alternative embodiments of the chemilumiscent applicator shown in FIGS. 2A and 2B.

In one alternative embodiment of a chemiluminescent applicator 400 shown in FIG. 3A, an enhancing attachment is coupled to the applicator housing 202. For example, the enhancing attachment can be a heating element 302, such as an electrical heating coil, a chemical heat source (not shown), or, more generally, any suitable thermal source. Enhancing the chemiluminescent mixture in this manner can be used to control the intensity and duration of the light dosage, by controlling the rate of a chemical reaction causing the chemiluminesence. In a second action, heating of the treatment site can further sensitize the target organism (i.e., *P. acnes*), thereby enhancing the therapeutic effect of the same dosage of light.

Figure 3B:
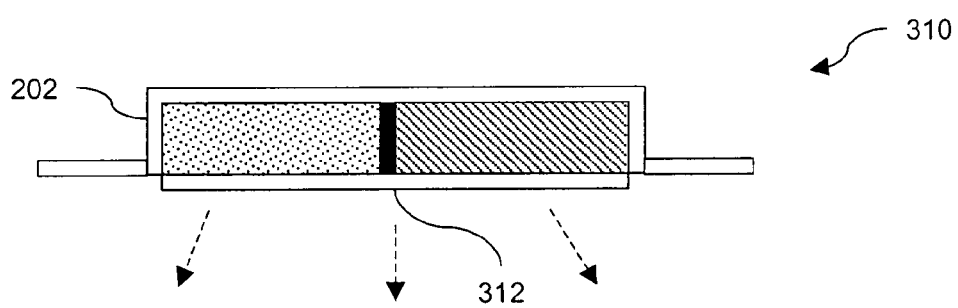

In an alternative embodiment shown in FIG. 3B, an applicator 310 further includes, placed between the applicator housing 202 and the treatment site, an additional component, such as a treatment pad 312. Generally, the treatment pad 312 is optically transmissive, at least over the intended wavelengths of operation, so as not to substantially absorb, or attenuate radiation from the chemilumiscent material. The treatment pad 312 can include additional treatment compounds, such as skin soothers, lotions, and/or one or more sensitizing drugs. Alternatively or additionally, the treatment pad 312 can include a filter for selecting a preferential wavelength, or wavelength region (e.g., transmitting visible light, while blocking ultraviolet light, or providing a blue/violet filter).

Generally, the bacteria can be subjected to certain environmental stresses to make them more susceptible to the light delivered. For example, the use of adjunct materials and other sensitizing means can increase the effectiveness of any available light source. Examples of sensitizing materials include riboflavin, 5-amino levulinic acid (ALA), porfimer sodium, and motexafin lutetium. Further, the bacteria, such as *H. pylori*, can be subjected to increased levels of oxygen so that the creation of oxygen radicals is more frequent, thereby creating more oxygen radicals for bacterial destruction. Bacteria are sensitive to their environment, and *H. pylori* is a sensitive bacterium. In vitro tests have revealed that the bacteria are sensitive to the level of iron available in the growth medium, the gas composition provided during growth, and even the length of time that the culture has been grown. Thus, modifying the local environment in the stomach can be used to facilitate the eradication by light by making the bacteria more fragile or susceptible. For example, techniques including ingestion or spraying of iodine or an iodine containing liquid like Lugol's solution, altering the pH levels, or increasing the temperature of the stomach, for example using hot water or some other means, can be used to compromise the bacteria's resistance to illumination.

Additionally, as bacteria require iron for robust replication, providing a patient with an iron chelating agent decreases the free iron available thereby making the bacteria more susceptible to the light treatment. Alternatively, the bacteria may be more susceptible just after replication. Thus, providing a source of free iron may make it more susceptible to eradication through light treatment. These and other means for making the bacteria more susceptible to light treatment can be used.

Figure 3C:
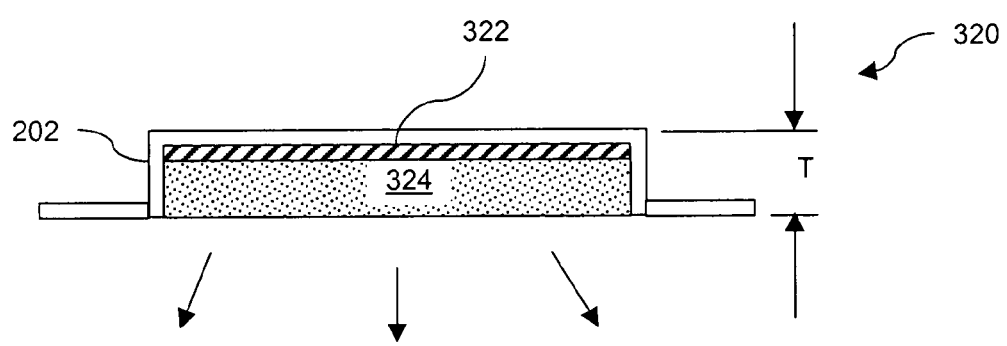

In some embodiments, an applicator 320 includes a reflector 322 to preferentially direct emitted radiation as shown in FIG. 3C. For example, the applicator housing 202 includes a reflective material 322 applied to an interior portion of the housing, opposite the side applied to the treatment site. Thus, as the chemiluminescent material 324 emits light in all directions, the reflector 322 redirects a portion of the light initially directed away from the treatment site, back toward the treatment site, effectively doubling the amount of light for the same volume of material 324. Again, as some of the light will be reabsorbed by the material itself, it is important to maintain a relatively small thickness, T.

Depending on the dosage requirements and the light yield of a particular chemiluminescent material, it may be necessary to exchange the chemiluminescent material illuminating the treatment site at a selected rate. For example, a material flow rate can be selected to maintain the light-emitting material exposed to the treatment site during its period of peak yield, then flowing the material away from the treatment site and replacing it with fresh material, again at its respective peak yield. Thus, the components are combined and mixed at a distant location and pumped through tubing or some other shaped container past the biological target for the treatment duration.

Figure 4A:
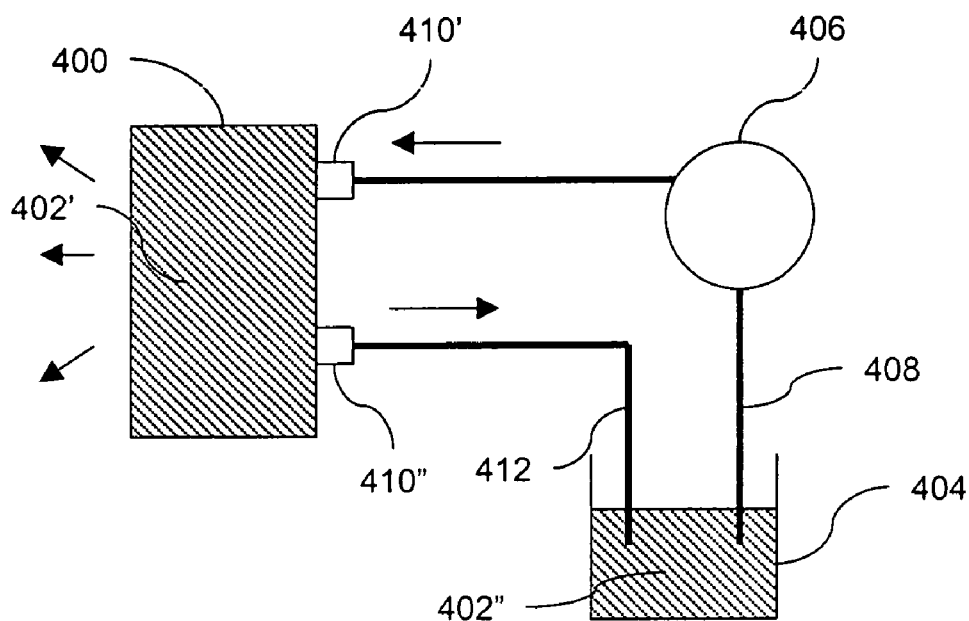
FIGS. 4A and 4B are schematic diagrams of alternative embodiments of the invention including an external reservoir for storing a portion of the chemiluminescent material.

Referring to FIG. 4A, a chemiluminescent applicator 400 includes within it a first portion of chemiluminescent material 402' proximate to the biological target. An external reservoir 404 includes a second portion of chemiluminescent material 402" away from the treatment site. A pump 406 connected to a first tube 408 between the reservoir 404 and the applicator 400, pumps a portion of the material 402" from the reservoir into the applicator 400 through a first port 410'. The influx of fresh material 402" into the applicator 400 causes a portion of the at least partially exhausted material 402' to exit through a second tube 412, connected to the applicator 400 at a second port 410".

Figure 4B:
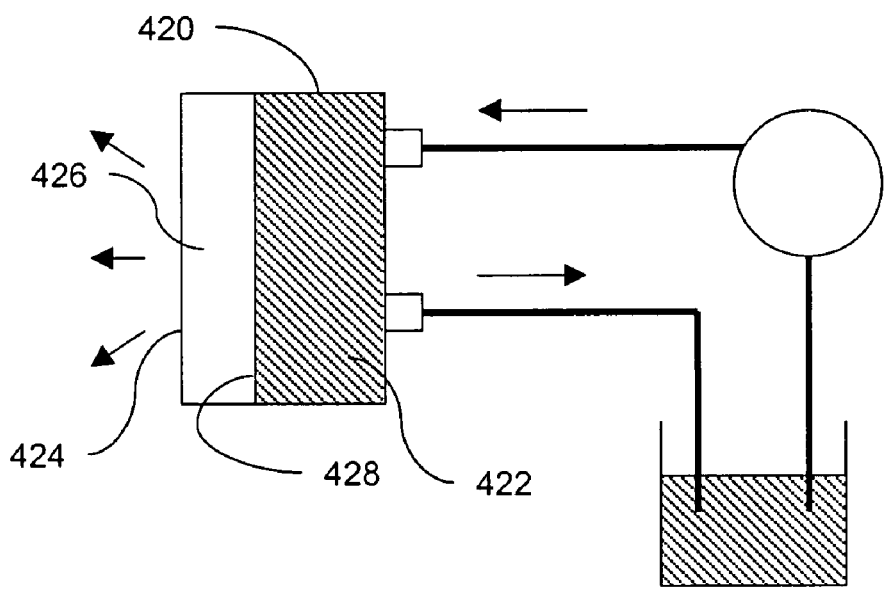

In another embodiment, referring to FIG. 4B, the chemiluminescent component materials are not directly mixed. Rather, an energizer material 422 is brought into close proximity with the wavelength-selectable material, resulting in the emission of light, without consuming any of the wavelength-selectable material 426. The pump 406 pumps the energizer component 422 from the reservoir to an energizer chamber 420 of the chemiluminescent applicator. The wavelength-selectable material 426 is disposed within a separate chamber 424 separated from the first chamber 420 by a barrier 428. As the energizer component expends its energy within the first chamber, it is replaced with fresh energizer component through the action of the pump.

In some embodiments, the component materials are combined at a distant location from the target biological material. The light produced from the remote chemiluminescent material is then transmitted to the biological target via an optical transmission device, such as a fiber optic guide.

Figure 5:
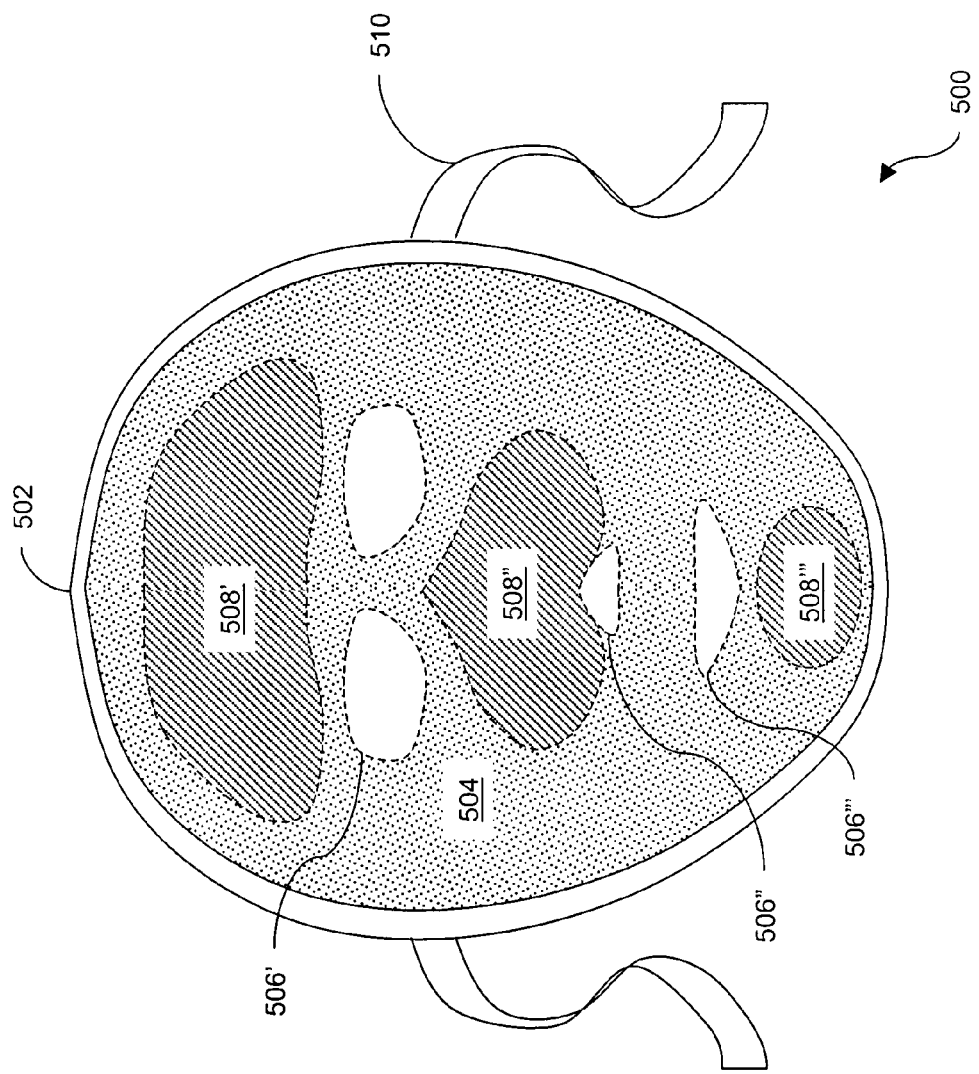
FIG. 5 is a schematic diagram of the invention showing an interior portion of one embodiment of a chemiluminescent applicator adapted for facial applications.

The invention can also be provided in a flexible container capable of being fitted to parts of the body to be treated. For example, referring to FIG. 5, a chemical containing housing is formed into a mask 500 for the face. The mask 500 includes a mask housing 502 that covers at least a portion of the face. The mask housing 502 includes two (or more) chemiluminescent chemical components on the interior surface 504 worn against the face. The chemical components are separated from each other by a breakable barrier (not shown). When broken, the chemicals mix together thereby initiating a chemical reaction that produces light. The chemicals can be disposed along the entire interior surface of the mask 504, or alternatively, along one or more selected sub-regions 508', 508", 508'" (generally 508). Alternatively, the chemical could be pre-mixed outside of the mask 500, the injected into the mask 500 through a fill port (not shown). A drain port (not shown) would also be required for embodiments in which the mask 500 is reused.

The mask 500 is worn for a period of time determined by the dosage—the necessary time to provide the desired dosage to the biological target for the given light intensity. The mask 500 can also include one or more apertures, as required, such as eye apertures 506', a nose aperture 506", and a mouth aperture 506'". Additionally, the mask 500 includes a fastening element, such as a strap 510, or band for tying or placing about the back of the head to secure the mask 500 to the face.

Figure 6B:
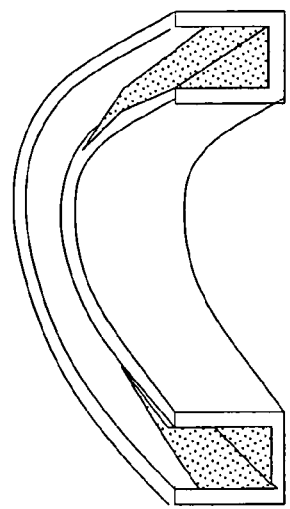
FIGS. 6A and 6B respectively show a schematic diagram and a perspective view of one embodiment of a chemiluminescent applicator adapted for oral applications.
Figure 6A:
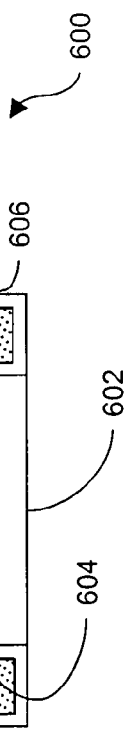

Another application is for chemiluminescent light therapy used within the oral cavity—an area difficult to treat effectively with a light source due to shadows created by the teeth and tongue. The use of a free-flowing light source that can be a liquid is a significant advantage in these applications. Whitening teeth by use of a brightening chemical and light in the 400–690 nm range can also be performed. The chemiluminescent material is particularly well suited for treating the mouth because it can be applied to bath the entire region in light at once, without shadows. For example, the material can be prepared as a rinse and held in the mouth for the treatment time. Alternatively, the material can be inserted into a mouth guard that can be temporarily applied to the teeth, thereby bathing the teeth in the chemiluminescent light for the treatment period. At least one beneficial effect of light treatment applied to the teeth includes whitening. FIGS. 6A and 6B show one embodiment of a mouth guard 600 including a housing 602 adapted for fitting about the teeth. The housing 602 includes an interior surface 604. The chemiluminescent material is then inserted into the interior portion 604 of the housing 602 and the housing applied to a patient's teeth for the treatment period.

One type of chemical system that emits chemiluminescence is an oxylate-ester system. In this reaction, two chemicals, an oxylate and a peroxide, are mixed to release energy. A portion of the energy released from this reaction excites a third (or fourth, etc.) chemical that is a fluorescent dye called a fluorophore. The dye is energized and as it releases its energy, photons are emitted. One embodiment of this system is to attach or immobilize the dye portion of the chemical system to the wall or other portion of the container and allow the energy producing chemicals to contact the dye. The energy producing chemicals can be replaced, replenished, or cycled past the dye for more light energy production.

In some embodiments, the fluorophore and or a peroxyoxalate ester, such as TCPO, can be immobilized on a substrate. For example, small diameter glass beads can be coated with a fluorophore. Chemiluminescence occurs when the coated beads are brought into contact with a fuel-oxidant mixture. Optionally, a solvent is added to slowly dissolve a coating (e.g., a fluorophore and or a peroxyoxalate ester, such as TCPO), thereby controlling the rate of reaction by controlling the release of the fluorophore into solution.

Alternatively, or in addition the fluorophore can be immobilized and separated from the energy producing chemicals by a barrier. For example, the barrier can include a thin transparent medium in direct contact with a circulating solution of fuel and oxidant. Since the fluorophore isn't actually consumed, this would permit continuous recycling of it. This will result in higher quantum yields because excitation of the dye would not necessarily be diffusion limited. Forcing the fuel/oxidant flow achieves higher replenishment rates of the excited intermediate in contact with the dye. This would also mediate any toxicity issues created by release of the dye. Another embodiment is to control the dye flow separately from the fuel/oxidant.

Figure 7:
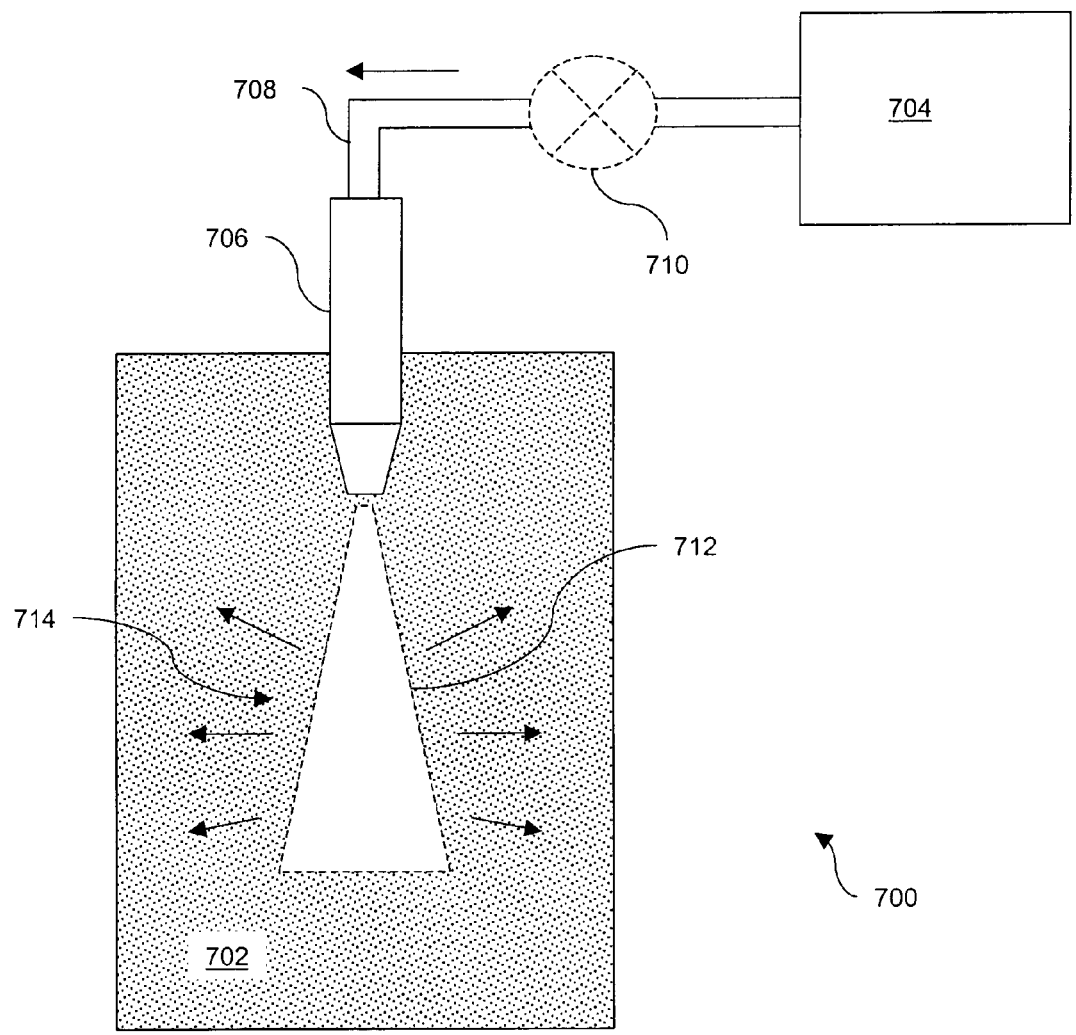
FIG. 7 is a schematic diagram of an embodiment of a chemiluminescent light source including a spray nozzle for directing the mixture of components of the chemiluminescent material.

For example, the dye solution can be sprayed into the fuel/oxidant mixture. By controlling the location where the dye enters the fuel/oxidant mixture, the location and extent of the chemiluminescent reaction can be controlled. FIG. 7 shows one embodiment of a spray system 700 including a first housing including a fuel/oxidant mixture 702. A second, remote vessel contains the dye 704. The second vessel is connected to a spray nozzle 706 through a hose 708. The hose optionally including a pump 710 to pump the dye from the remote vessel to the nozzle 706. If a pump 710 is not provided, the dye flow could be induced by increasing pressure upon the remote vessel.

A resulting dye jet stream 712 could be shaped at will, by adjusting the nozzle 706, flow characteristics, and fluid properties. In this way luminescence could be induced when and where desired (e.g., the localized region 714 about the jet stream 712).

A chemiluminescent light source is generally a smaller, less expensive alternative to other conventional light sources. Chemiluminescent light sources can even be prepared as a disposable light sources, well suited for intimate contact with a patient's body, without a need to re-sterilize between uses. Further, chemiluminescent light sources can be prepared to selectably emit substantially within certain wavelength regions, or bands. The ability of the liquid to conform in a pouch to irregular surfaces makes it particularly convenient.

This light treatment source can be used for various applications in medicine. One application is for treatments of wounds, particularly for speeding the healing of wounds. It has been shown that daily exposure of wounds with 1 Joule/cm$^2$ of light at 633 nm promotes collagen production. This speeds and aids in wound healing. The use of chemiluminescence as a light source allows for increasing the time of light treatment.

Figure 8:
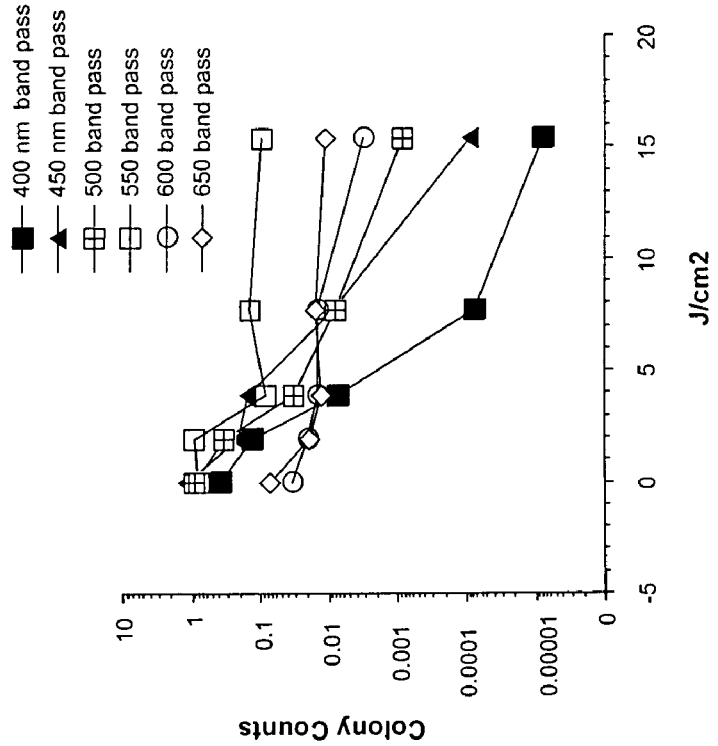
FIG. 8 is a graph showing test results measuring the effectiveness of *H. pylori* treatment versus light intensity.

Test results have been plotted to illustrate the effectiveness of light at different wavelengths and intensities. FIG. 8 shows the *H. pylori* colony forming units along the vertical axis versus the light intensity along the horizontal axis. The lower colony counts reflect a more effective treatment. Additionally, multiple curves are plotted together with each curve representing test results for a illumination by light of a different wavelength. In general, all curves show increasing effectiveness with increasing intensity. Further, light in the blue/violet spectrum (400 nm to 450 nm), generally are more effective than the other wavelengths tested.

In an exemplary treatment of an *H. pylori* infection within the interior of a patient's stomach, a solution-phase chemiluminescent reaction is prepared (e.g., a solution of luminol and excess $H_2O_2$) emitting visible light having wavelengths in the 405 to 415 nm range. The chemical reaction produces a light energy intensity between 10 and 100 Joules/cm$^2$. For a stomach having an interior surface area of approximately 800 cm$^2$, the total energy requirement is approximately 8,000 to 80,000 Joules. To meet the energy requirements of an effective treatment, a dynamic flow chemiluminescent system is used. Thus, a chemiluminescent reaction is prepared externally and injected into the patient's stomach where peak light emission occurs. As the chemiluminescent reaction slows, the reactants are extracted from the patient's stomach to be replaced with fresh reactants. A delivery device, or vessel, such as a balloon having an entry and exit tube can be used to control the flow of the reactants.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. An apparatus for killing and/or debilitating pathogenic microorganisms in or on a body comprising a chemiluminescent light source providing electromagnetic radiation having predetermined wavelengths in the visible spectrum selected for absorption by naturally-occurring photosensitive chemicals produced by the body;
   wherein the chemiluminescent light source comprises:
      an energizer producing a selected amount of energy for a selected duration;
      a wavelength-selectable material energetically coupled to the energizer for producing electromagnetic radiation in response to the coupled energy at one or more selected wavelengths for the selected duration;
      a first reservoir configured to be initially containing the wavelength-selectable material, the first reservoir electromagnetically coupled to a treatment site;
      a second reservoir containing the energizer;
      a nozzle for coupling the second reservoir to the first reservoir; and
      means for transporting at least a portion of the energizer from the second reservoir to the first reservoir through the nozzle.

2. The apparatus of claim 1, wherein the nozzle is adjustable.

3. An apparatus for killing and/or debilitating pathogenic microorganisms in or on a body comprising a chemiluminescent light source providing electromagnetic radiation having predetermined wavelengths in the visible spectrum selected for absorption by naturally-occurring photosensitive chemicals produced by the body;
   wherein the chemiluminescent light source comprises:
      an energizer producing a selected amount of energy for a selected duration; and
      a wavelength-selectable material energetically coupled to the energizer for producing electromagnetic radiation in response to the coupled energy at one or more selected wavelengths for the selected duration;
   wherein the energizer comprises an energy-releasing chemical reaction;
   wherein the energy-releasing chemical reaction comprises an oxalate and a peroxide that, when mixed together, release energy.

4. An apparatus for killing and/or debilitating pathogenic microorganisms in or on a body comprising a chemiluminescent light source providing electromagnetic radiation having predetermined wavelengths in the visible spectrum selected for absorption by naturally-occurring photosensitive chemicals produced by the body;
   wherein the chemiluminescent light source comprises a liquid;
      a first reservoir configured to be containing a first portion of the liquid electromagnetically coupled to a treatment site;
      a second reservoir containing a second portion of the liquid remotely located from the treatment site;
      a tube coupled between the first and second reservoirs; and
      means for transporting through the tube at least some of the first portion of the liquid from the first reservoir to the second reservoir.

* * * * *